(12) United States Patent  
Fujieda

(10) Patent No.: US 7,284,861 B2  
(45) Date of Patent: Oct. 23, 2007

(54) OPHTHALMIC APPARATUS AND CORNEAL SURGERY APPARATUS

(75) Inventor: Masanao Fujieda, Toyohashi (JP)

(73) Assignee: Nidek Co., Ltd (JP)

( * ) Notice: Subject to any disclaimer, the term of this patent is extended or adjusted under 35 U.S.C. 154(b) by 674 days.

(21) Appl. No.: 10/307,356

(22) Filed: Dec. 2, 2002

(65) Prior Publication Data

US 2003/0120266 A1 Jun. 26, 2003

(30) Foreign Application Priority Data

Dec. 3, 2001 (JP) ............................. 2001-369261

(51) Int. Cl.
*A61B 3/11* (2006.01)
*A61B 3/14* (2006.01)

(52) U.S. Cl. ...................... 351/206; 351/209

(58) Field of Classification Search ................ 351/200, 351/204, 205, 206, 208, 209, 212, 221, 246; 606/4–6, 10; 607/53, 54
See application file for complete search history.

(56) References Cited

U.S. PATENT DOCUMENTS

| | | | |
|---|---|---|---|
| 5,632,742 A | 5/1997 | Frey et al. | |
| 5,637,109 A | 6/1997 | Sumiya | |
| 5,740,803 A * | 4/1998 | Gray et al. | 351/212 |
| 5,907,388 A | 5/1999 | Fujieda | |
| 6,033,075 A | 3/2000 | Fujieda et al. | |
| 6,086,204 A | 7/2000 | Magnante | |
| 6,159,202 A | 12/2000 | Sumiya et al. | |
| 6,299,311 B1 | 10/2001 | Williams et al. | |
| 6,322,216 B1 | 11/2001 | Yee et al. | |
| 6,413,251 B1 * | 7/2002 | Williams | 606/5 |
| 6,598,971 B2 * | 7/2003 | Cleveland | 351/209 |
| 2003/0176855 A1 * | 9/2003 | Gross et al. | 606/5 |
| 2004/0169817 A1 * | 9/2004 | Grotehusmann et al. | 351/204 |

FOREIGN PATENT DOCUMENTS

| | | |
|---|---|---|
| EP | 0850614 A2 | 7/1998 |
| EP | 1 138 290 A1 | 10/2001 |
| EP | 1153584 A1 | 11/2001 |

OTHER PUBLICATIONS

Partial European Search Report dated May 22, 2003.
EPO Search Report Oct. 16, 2003.

* cited by examiner

*Primary Examiner*—Scott J. Sugarman
(74) *Attorney, Agent, or Firm*—Rader Fishman & Grauer PLLC; Ronald P. Kananen

(57) ABSTRACT

An ophthalmic apparatus for obtaining differences between the pupil positions in photopia and scotopia accurately, and a corneal surgery apparatus for ablating a cornea of an eye by laser beam irradiation allowing for the differences. The ophthalmic apparatus has devices for inputting a first image of an anterior eye segment in photopia and a second one in scotopia, for obtaining pupil information in the images and differences between the pupil information in photopia and that in scotopia, and for outputting the differences. The corneal surgery apparatus has devices for irradiating the cornea with a laser beam, for aligning an irradiation position with the eye, for inputting differences between the pupil positions in photopia and scotopia, for detecting the photopic pupil position, for obtaining an alignment position of the laser beam based on the pupil position and the positional difference, and for controlling the alignment device based on the alignment position.

6 Claims, 8 Drawing Sheets

OPHTHALMIC APPARATUS AND CORNEAL SURGERY APPARATUS

BACKGROUND OF THE INVENTION

1. Field of the Invention

The present invention relates to an ophthalmic apparatus and a corneal surgery apparatus used in ophthalmic clinics and the like.

2. Description of Related Art

On ophthalmic diagnosis, examination, treatment and prescription, it is sometimes necessary to obtain information about the position and/or shape of a pupil. For example, in corneal surgery for correcting refractive power by ablating a cornea with a laser beam, it is common practice to align a reference axis of irradiation of the laser beam with the position of a pupil center.

In addition, among multifocal contact lenses, in which different lens diopters are provided in the form of concentric circles around an axis of an optical center of the lens, there are some in which the axis of the optical center is decentered with respect to the geometric center of the lens. The amount of the decentering is determined in consideration of the pupil center position.

By the way, in the above-mentioned corneal surgery, a surgeon performs surgery in a well-lighted surgery room while observing a patient's eye illuminated with visible light. In this case, the patient's eye is in photopia (photopic vision) (i.e. the pupil of the eye is constricted), and the laser-beam irradiation is performed in alignment with the pupil center position in photopia. However, there are some cases where the pupil center position in photopia is not necessarily equal to that in scotopia (i.e. the pupil of the eye is dilated) according to individual circumstances. Conventionally, the differences (variances) between the pupil center position in photopia and that in scotopia are not taken into account. Therefore, the laser irradiation based on the pupil center position of the eye in photopia tends to cause a halo or glare when the eye is in scotopia.

Also, when designing a multifocal contact lens as described above, it has not been taken into account that the pupil center position in photopia is different from that in scotopia.

SUMMARY OF THE INVENTION

The present invention has been made in view of the above circumstances and has an object to overcome the above problems and to provide an ophthalmic apparatus capable of obtaining information about the differences between the pupil information in photopia and that in scotopia with unerring accuracy and a corneal surgery apparatus capable of performing surgery in consideration of the pupil information and/or the information about the differences.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprises input means for inputting a first image of an anterior segment of a patient's eye in photopia and a second image of the anterior segment of the eye in scotopia, a pupil information computation unit which obtains, by image processing, pupil information including at least one of a position of a pupil of the eye and a shape of the pupil in each of the inputted images, and obtains information about a difference between the pupil information in the first image and that in the second image, and output means for outputting the obtained information about the difference.

In another aspect of the present invention, a corneal surgery apparatus for ablating a cornea by laser beam irradiation comprises a laser irradiation unit which irradiates a cornea of a patient's eye with a laser beam, the irradiation unit including an optical system, an alignment unit which aligns an irradiation position of the laser beam with the eye, position input means for inputting information about a positional difference between a pupil position of the eye in photopia and a pupil position of the eye in scotopia, a pupil position detection unit which detects a pupil position of the eye in photopia by image processing, the pupil position detection unit including an image pickup element which obtains an image of the eye in photopia through image-pickup, a position computation unit which obtains information about an alignment position of the laser beam based on the detected pupil position and the inputted information about the positional difference, and an alignment control unit which controls the alignment unit based on the obtained information about the alignment position.

Yet, in another aspect of the present invention, a corneal surgery apparatus for ablating a cornea by laser irradiation comprises a laser irradiation unit which irradiates a cornea of a patient's eye with a laser beam, the irradiation unit including an optical system, shape input means for inputting a pupil shape of the eye in photopia and a pupil shape of the eye in scotopia, an area computation unit which obtains a size of an ablation area based on each of the inputted pupil shapes, and an irradiation control unit which controls the irradiation unit based on the obtained size of the ablation area.

According to the present invention described above, the information about the differences between pupil information in photopia and that in scotopia may be obtained with unerring accuracy. The pupil information and/or the information about the differences thus obtained may therefore be utilized for refractive surgery and design of a contact lens.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1B:
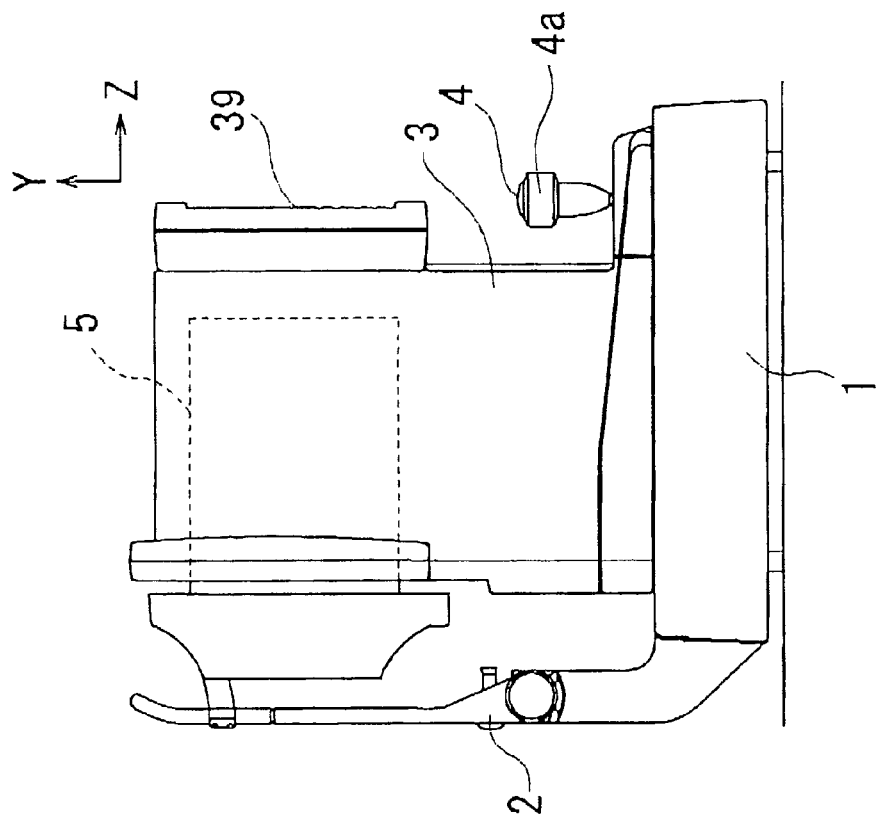
FIGS. 1A and 1B are views schematically showing an external configuration of an ophthalmic apparatus consistent with the present invention.
Figure 1A:
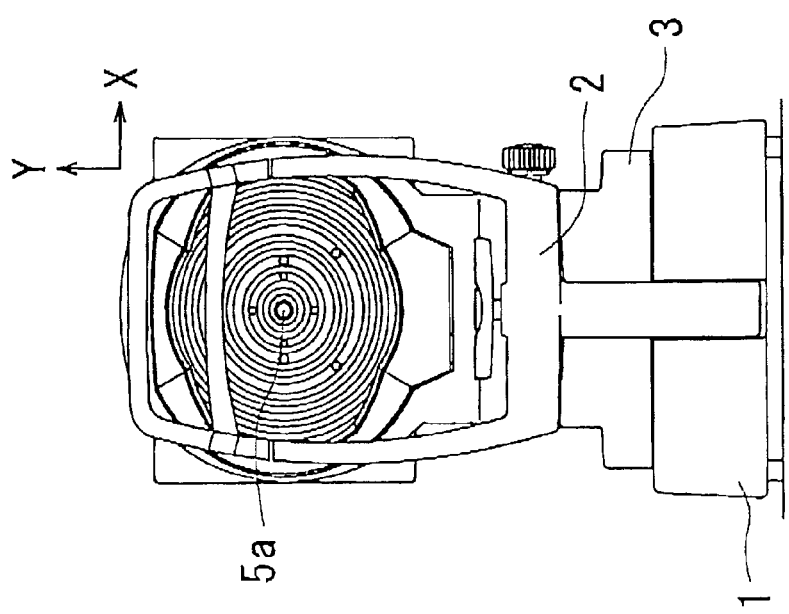

A detailed description of one preferred embodiment of an ophthalmic apparatus and a corneal surgery apparatus embodying the present invention will now be given referring to the accompanying drawings. FIGS. 1A and 1B are views schematically showing an external configuration of the ophthalmic apparatus consistent with the present invention; FIG. 1A is a front view seen from an examinee's side, and FIG. 1B is a side view.

On a fixation base 1, a head supporting part 2 is mounted securely in order to fix the examinee's head. In a measurement part 5, optical systems and other systems are stored. A measurement window 5a through which light passes is provided approximately at the lateral center on the side facing the examinee. When a joystick 4 is tilted backward/forward and rightward/leftward, a main body 3 incorporating the measurement part 5 slides and moves backward/forward and rightward/leftward (in Z and X directions) on the fixation base 1. In addition, when a rotation knob 4a provided on the joystick 4 is rotated, a Y(up-and-down)-direction driving device constituted of a motor and the like is actuated to move the measurement part 5 up and down (in a Y direction) with respect to the main body 3.

On a color monitor 39, an image of an anterior segment of a patient's eye is displayed for observation, along with alignment information, a measurement result, and other information to be indicated to an examiner.

Figure 2:
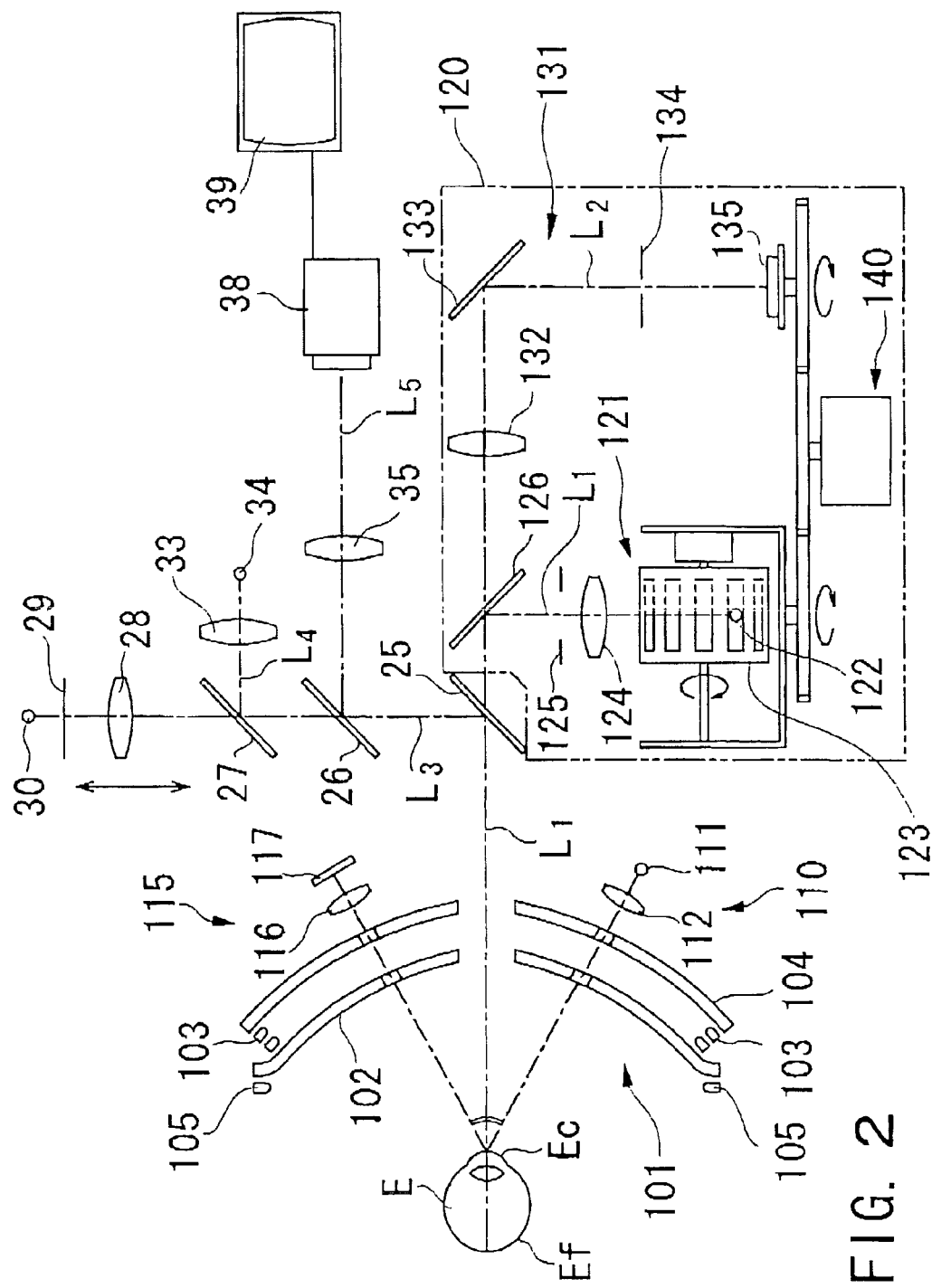
FIG. 2 is a view schematically showing a structure of an optical system included in the ophthalmic apparatus.

FIG. 2 is a view schematically showing the structure of the optical systems stored in the measurement part 5. An optical system 101 is used to irradiate (project) light for measuring a corneal shape. A placido disc 102 and a reflecting plate 104 are approximately dome-shaped, and have apertures at their centers. On the disc 102, a pattern of rings including a multitude of light-transmitting parts and light-shielding parts is formed in concentric circles around an optical axis L1. A light source 103 such as an LED emits visible light, which is then reflected by the reflecting plate 104 to illuminate the placido disc 102 from behind approximately uniformly. An image of the ring pattern is formed on a cornea Ec of a patient's eye E. An anterior-segment illumination light source 105 emitting near-infrared light is provided on the rim of the placido disc 102.

Placed behind the reflecting plate 104 are an optical system 110 used to irradiate (project) near infrared light as a target (index) for alignment in a working distance direction, which has a light source 111 and a lens 112, and an optical system 115 used to detect an image of the target, which has a lens 116 and a position-detecting element 117. The near-infrared light emitted from the light source 111 is changed into approximately parallel light via the lens 112. The light passes through the apertures provided in the reflecting plate 104 and the placido disc 102 respectively, and is then applied to the cornea EC from an oblique direction, thereby forming the target image on the cornea Ec. The light of the target image formed on the cornea Ec passes through the apertures provided in the placido disc 102 and the reflecting plate 104, and enters the position-detecting element 117 via the lens 116. Based on the position of the target image light having entered the position-detecting element 117, alignment condition in the working distance direction of the apparatus with respect to the eye E is detected.

An eye refractive power measurement optical system 120 is provided behind the reflecting plate 104. The eye refractive power measurement optical system 120 is composed of a slit light irradiating (projecting) optical system 121 and a slit image detecting optical system 131. Near infrared light emitted from a light source 122 illuminates a slit aperture provided in a rotation sector 123. The slit light scanned by rotation of the rotation sector 123 passes through a lens 124 and a diaphragm 125, and is then reflected by a half mirror 126. Thereafter the slit light passes through a dichroic mirror 25, converges in the vicinity of the cornea Ec, and is then irradiated (projected) onto a fundus Ef of the eye E.

The half mirror 126 makes the optical axis L1 of the lens 124 coaxial with an optical axis L2 of a photo-receiving lens 132. The dichroic mirror 25 makes the optical axis L1 coaxial with an optical axis L3 of a lens 28.

Figure 4:
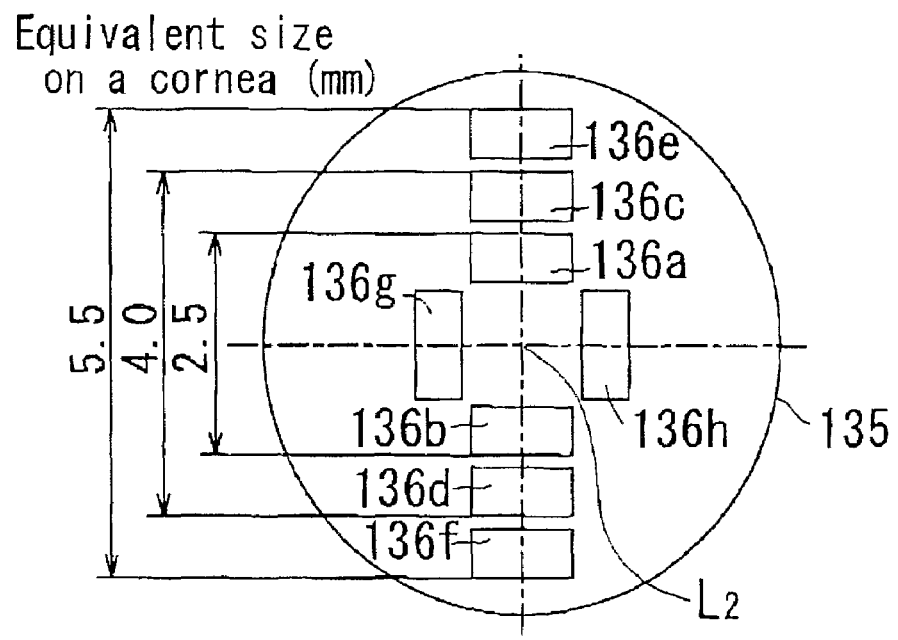
FIG. 4 is a view showing an arrangement of photo-receiving elements.

A diaphragm 134 is placed at the back focal position of the lens 132. A photo-receiving part 135 has a photo-receiving surface on which eight photo-receiving elements 136a to 136h are arranged in the positions approximately conjugate with the cornea Ec with respect to the lens 132. Among them, the photo-receiving elements 136a to 136f are positioned on a straight line passing through the center of the photo-receiving surface (the optical axis L2), and each pair of the photo-receiving elements 136a and 136b, 136c and 136d, and 136e and 136f are disposed symmetrically with respect to the center of the photo-receiving surface. The distance between the photo-receiving elements arranged in three pairs are set so as to obtain refractive power at the positions corresponding to those elements in a meridian direction on the cornea (each of the distances in FIG. 4 is shown as an equivalent size on the cornea). On the other hand, the photo-receiving elements 136g and 136h are disposed symmetrically with respect to the center of the photo-receiving surface on a straight line perpendicular to the straight line of the photo-receiving elements 136a to 136f.

The slit light reflected from the fundus Ef passes through the dichroic mirror 25, the half mirror 126 and the lens 132, is reflected by a mirror 133, passes through the diaphragm 134, and is then received by the photo-receiving part 135.

In the eye refractive power measurement optical system 120, a rotation mechanism 140 constituted of a motor, a gear and the like rotates the rotation sector 123 and the photo-receiving part 135 in synchronism about their respective optical axes.

On the optical axis L3, half mirrors 26 and 27, a a fixation target plate 29, and a light source 30 for eye-fixation are placed. The fixation target plate 29 has a fixation point as a target (index) for eye-fixation at its center, and the periphery of that point on the plate 29 is configured to transmit visible light emitted from the light source 30. The light emitted from the light source 30 is irradiated (projected) onto the eye E via the plate 29, the lens 28, the half mirrors 27 and 26, and the dichroic mirror 25. The lens 28, which is movable in the direction of the optical axis L3 to change the position of the fixation point, fogs the eye E at the time of eye refractive power measurement, or applies accommodation load.

On an optical axis L4 of a lens 33 made coaxial with the optical axis L3 by the half mirror 27, a light source 34 for alignment is placed, and near infrared light as a target (index) for alignment in vertical and lateral directions is irradiated (projected) onto the cornea Ec when the light source 34 lights up.

In addition, on an optical axis L5 of a lens 35 made coaxial with the optical axis L3 by the half mirror 26, a CCD camera 38 as an image pickup element is placed, and the camera 38 receives the light reflected from the eye E. The output from the camera 38 is inputted to a monitor 39, on which a picked-up image is then displayed. The camera 38 is used for obtaining the anterior segment image for observation, detecting the ring pattern image, and detecting an image of the target for alignment in the vertical and lateral directions.

Figure 3:
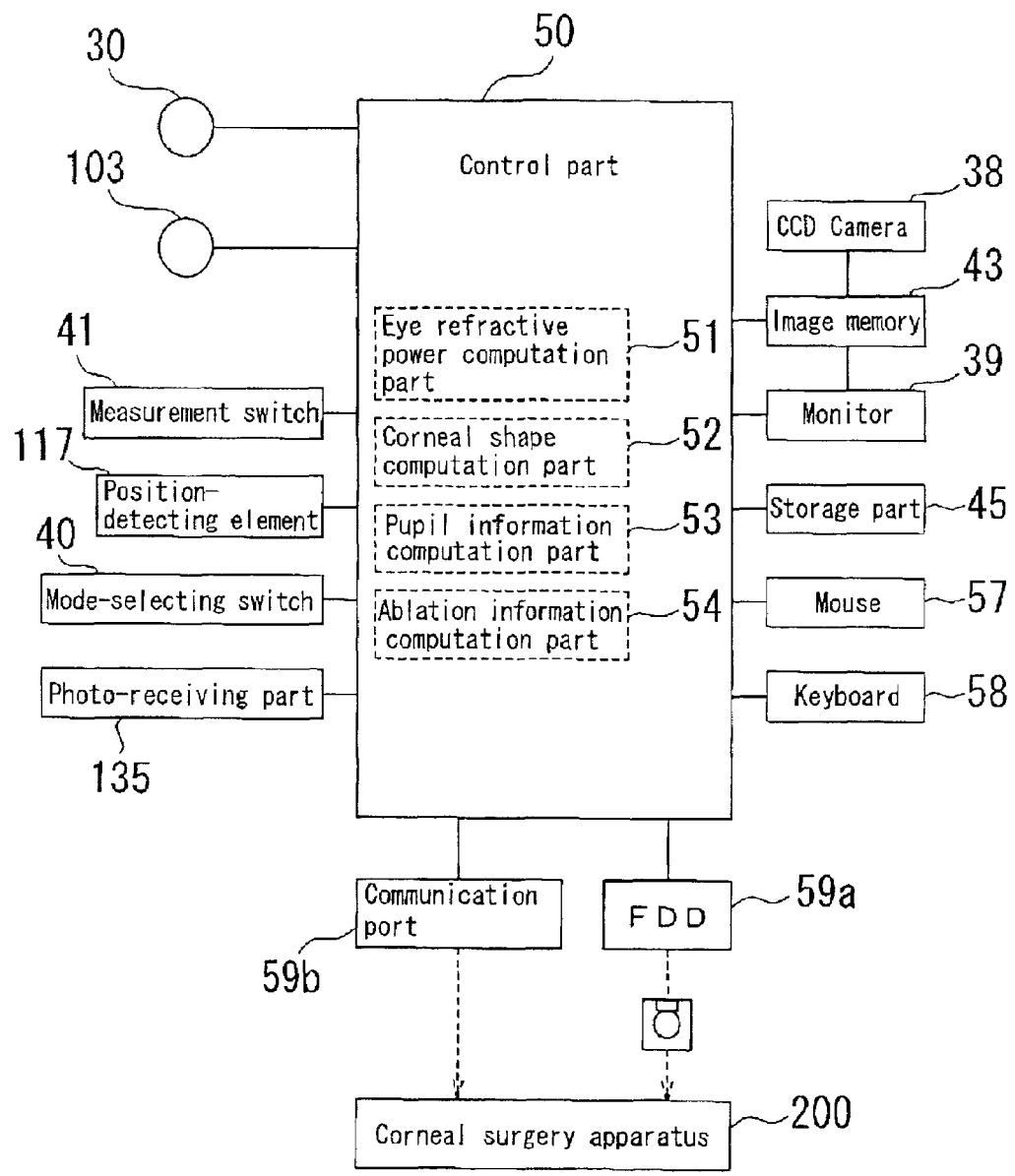
FIG. 3 is a block diagram schematically showing a control system included in the ophthalmic apparatus.

Next, the operation of the apparatus will now be described referring to a block diagram schematically showing a control system shown in FIG. 3. The present apparatus measures a corneal shape and eye refractive power, and computes corneal ablation information (data) for refractive surgery based on the data obtained from both measurements. In addition, the present apparatus also computes pupil information including the position of a pupil center and the shape of the pupil in photopia and those in scotopia, and then information about differences (variances) between the pupil information in photopia and that in scotopia. When ablation is performed using a corneal surgery apparatus, the pupil information and/or the difference information are used as information for determining the position at which a laser beam is aligned with the eye E (information for correcting the alignment position)

First, the operation performed at the time of eye refractive power measurement will now be described. A mode-selecting switch 40 is used to select a refractive power measuring mode.

Figure 5:
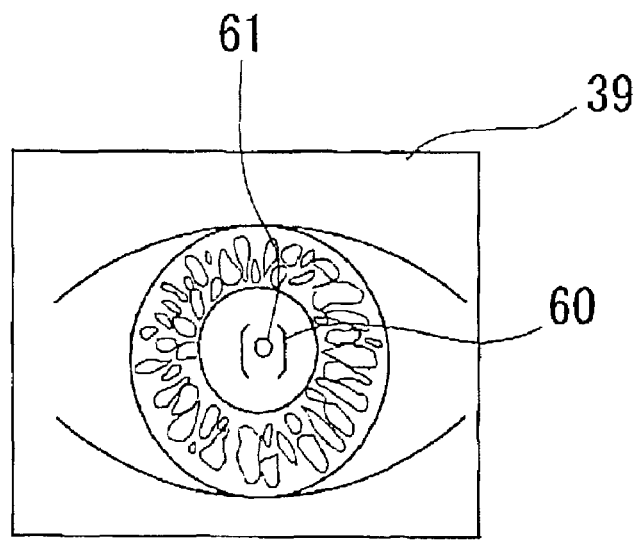
FIG. 5 is a view showing a method for performing alignment using an image of an anterior segment of an eye displayed on a monitor.

An examiner makes the patient to gaze at the fixation point illuminated by the light source 30, and moves the measurement part 5 in the X, Y and Z directions by operating the joystick 4 and the like to performs alignment, while observing the anterior segment image of the eye E displayed on the monitor 39 shown in FIG. 5. The alignment in the X and Y directions is performed so that an alignment target image 61 that the light source 34 forms at an optical center defined by a corneal optical system of the eye E is positioned at the center of an aiming marker 60 (see FIG. 5) displayed on the monitor 39 (hereinafter, the above-mentioned optical center will be referred to as a corneal center of the eye E, but it can be regarded as approximately a center of a visual axis of the eye E.) The aiming marker 60 displayed on the monitor 39 may be formed electrically, and adjustments are made in advance so that the center of the aiming marker 60 may coincide with an image-pickup optical axis (measurement optical axis) of the camera 38. The image-pickup optical axis is made coaxial with the optical axis L5. For the alignment in the Z direction, based on information about deviation in the working distance direction, which is obtained by the position-detecting element 117, a control part 50 performs control to display an indicator for working distance alignment on the monitor 39. With reference to this indicator, the examiner moves the main body 3 in the Z direction to make working distance alignment.

Once the alignment has been completed, the examiner depresses a measurement switch 41. Then, the measurement of eye refractive power is performed by the eye refractive power measurement optical system 120, and the anterior segment image of the eye E picked up by the camera 38 immediately before or after that measurement is stored in an image memory 43. An eye refractive power computation part 51 obtains a distribution of eye refractive power based on the phase difference between the output signals from each of the photo-receiving elements included in the photo-receiving part 135. For more details about the measurement of an eye refractive power distribution, U.S. Pat. No. 5,907,388 (corresponding to Japanese Patent Application Unexamined Publication No. Hei 10-108837) should be referred to, which describes basically the same measurement.

The anterior-segment image stored in the image memory 43 at this point is an image of the anterior segment of the eye E of which the pupil is dilated (in scotopia). During the measurement of eye refractive power, in order to obtain a refractive power distribution of wide range, it is preferred that the pupil should be wide open under the condition of natural mydriasis in a dark place where the letters in a newspaper are barely readable. In addition, the light intensity of the light source 30 which presents the fixation point should be adjusted for brightness so that the eye E may visually identify the fixation point, and should also be adjusted (reduced) so that myosis will not occur. The control part 50 adjusts the light intensity of the light source 30.

Next, a description will be given to the operation performed at the time of corneal shape measurement. Prior to the measurement, a corneal shape measurement mode is selected using the mode-selecting switch 40. The examiner performs alignment in the same manner as the eye refractive power measurement while looking at the monitor 39 to observe the anterior-segment image of the eye E which is illuminated by the light source 105.

After completion of the alignment, when the measurement switch 41 is depressed, the light source 103 is lit for a predetermined time to project light of the ring pattern onto the cornea Ec. Here, the light source 30 is lit at the maximum intensity of light. The anterior segment image in which the ring pattern image is formed is picked up by the camera 38, and is stored in the image memory 43. Since the light from the light source 103 and that from the light source 30 are both visible, the pupil of the eye E is constricted when the light source 103 and the light source 30 light up. The anterior segment image in photopia may be an image in which the ring pattern image is formed. However, the light source 103 may be turned off immediately after the ring pattern image is picked up, and then the anterior segment image in photopia may be obtained separately from the image for the corneal shape measurement. The light source 103 is kept lighted in view of the time for the pupil to be constricted. The anterior segment image in photopia with the pupil constricted is stored in the image memory 43.

It should be noted that, preferably, the light intensity of the light sources 103 and 30 giving visible stimulating light to the eye E at this point of time is adjusted to the extent of bringing the pupil into the same myotic condition as that required to perform refractive surgery using a corneal surgery apparatus which will be described below.

A corneal shape computation part 52 conducts image processing on the ring pattern image stored in the image memory 43, and detects the edges of the ring pattern image. Then, the corneal shape computation part 52 obtains the position of each edge relative to the corneal center for each step of a predetermined angle (1 degree), thereby obtaining a distribution of corneal curvature.

Once the data have been obtained from the measurements of the distributions of eye refractive power and corneal curvature both concerning the same eye E, a keyboard 58 or a mouse 57 connected to the control part 50 are operated in accordance with instructions displayed on the monitor 39 in order to input data about the size of an ablation area, a correction amount and the like. An ablation information computation part 54 computes corneal ablation information (data) such as an ablation amount based on the data from both the measurements and the inputted data. For more details about this computation, see U.S. Pat. No. 6,033,075 (corresponding to Japanese Patent Application Unexamined Publication No. Hei 11-342152). These measurement data and a result of the computation of the corneal ablation information are displayed on the monitor 39.

In the foregoing description, the distribution of eye refractive power is measured, but a distribution of wave aberration may be measured instead (as disclosed in U.S. Pat. No. 6,086,204). The distribution of eye refractive power may be replaced with the distribution of wave aberration, meaning that both are equivalent.

Figure 6:
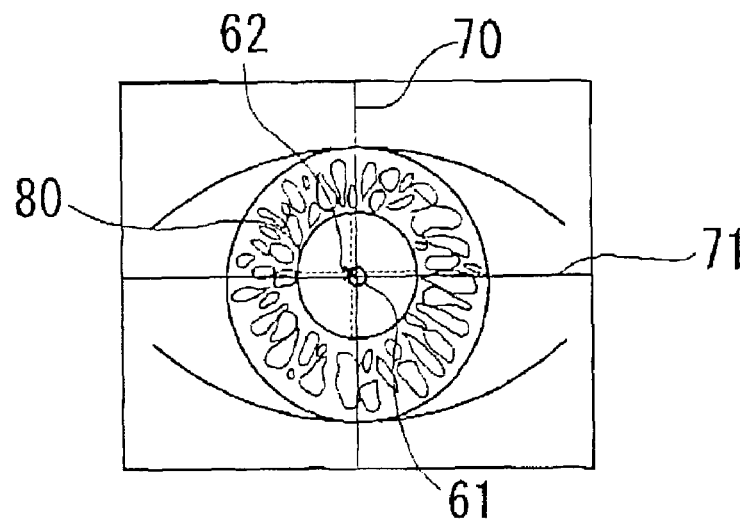
FIGS. 6A and 6B are views showing a method for obtaining the position of the pupil center from the picked-up image of the anterior segment of the eye.
Figure 6:
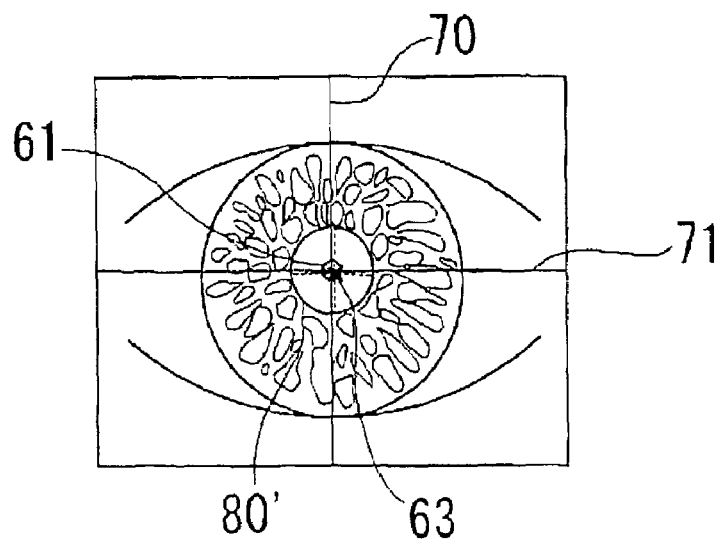

In addition, once the anterior segment image in photopia and that in scotopia are both obtained, a pupil information computation part 53 conducts image processing on each of the photopic and scotopic anterior-segment images stored in the image memory 43, and thereby obtains the pupil position (the pupil center position) and the pupil shape in each of the images. FIGS. 6A and 6B show a method by which the pupil information computation part 53 obtains the pupil center position in photopia and that in scotopia, and thus obtains the information for determining the alignment position (the information for correcting the alignment position).

FIG. 6A shows the scotopic anterior segment image picked up at the time of the eye refractive power measurement. The pupil information computation part 53 detects the edge of a pupil 80 based on a distribution of light intensity in the anterior-segment image, thereby obtaining the shape of the pupil 80. In addition, the pupil center position may be obtained as an intersection point of two midpoints between the pupil edges, one of which is on a lateral detection line 71 and the other on a vertical detection line 70 both passing through the center of the alignment target image 61 for alignment in the vertical and lateral directions. Reference numeral 62 denotes the obtained pupil center position. The pupil information computation part 53 detects the center of the alignment target image 61, and then obtains information about the pupil center position 62 with respect to the detected center of the alignment target image 61.

FIG. 6B shows the photopic anterior segment image. In a like matter, the pupil information computation part 53 obtains the shape of a pupil 80' based on the edge of the pupil 80' in photopia, and detects the alignment target image 61 to obtain the pupil center position 63, thereby obtaining the information about the pupil center position 63 with respect to the alignment target image 61.

Incidentally, for the detection of the pupil center position, it is preferred to average a plurality of positional coordinates of pupil edges specified in the vicinity of the lateral and vertical detection lines intersecting at the center of the alignment target image 61. In addition, alternative vertical and lateral detection lines which intersect at the center of the image may be specified to obtain the pupil edges, thus obtaining the pupil center position. Alternatively, the outline of the pupil may be obtained in advance by image processing, and the pupil center position may be obtained as an intersection point of the diagonal lines of a square circumscribing that outline.

In addition, when the corneal center of the eye E is completely aligned with the image-pickup optical axis, if both purely coincide with each other, the alignment target image 61 does not necessarily have to be detected. In this case, the pupil center position 62 and/or the pupil center position 63 may be obtained with respect to a predetermined position such as the center of the image. To be more specific, it is such a case where an automatic alignment mechanism is adopted.

Next, the pupil information computation part 53 compares the pupil center positions 62 and 63 with respect to the alignment target image 61, and obtains an amount of deviation (information about differences) of the scotopic pupil center position 62 from the photopic pupil center position 63. The deviation amount may be obtained as curvilinear coordinates, XY coordinates or others, of which the origin point is at the pupil center position 63. The deviation amount obtained is stored in a storage part 45 as the information for correcting the alignment position.

Figure 7:
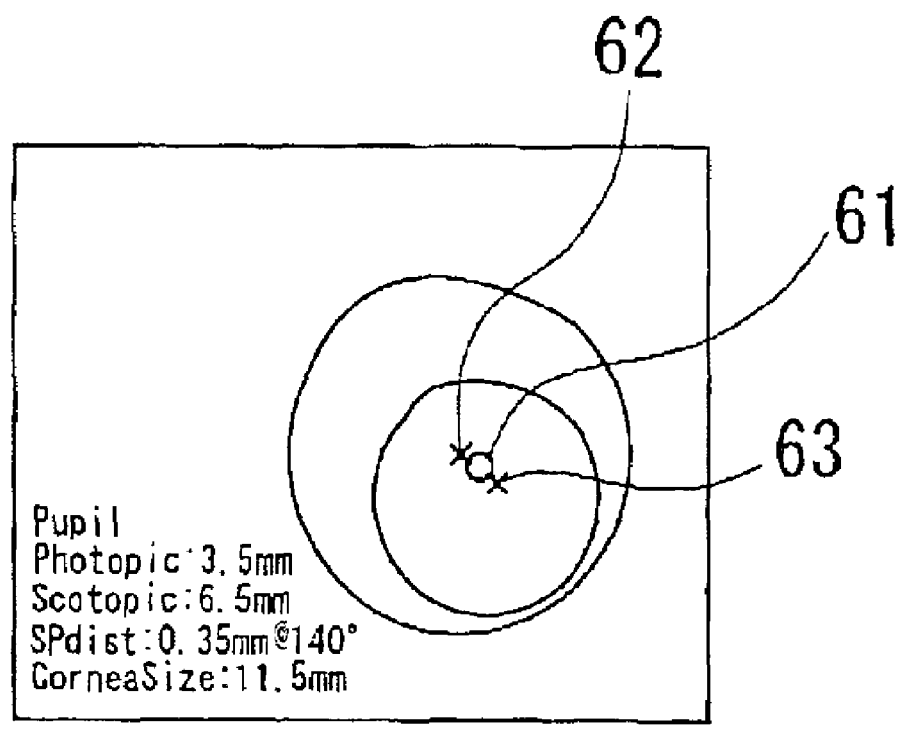
FIG. 7 is a view showing an example of displaying a difference between the pupil center position in photopia and that in scotopia.

In addition, information about the pupil in scotopia and that in photopia is displayed on the monitor 39. In other words, at this point, the pupil center positions 62 and 63 and/or the pupil edge in scotopia and that in photopia are graphically displayed on the monitor 39 to visually indicate the differences (variances) between the pupil center position and pupil shape in scotopia and those in photopia. FIG. 7 is an example of such display, where a line of the pupil edge in scotopia and that in photopia are graphically displayed based on the anterior segment image in photopia. A reference point for aligning them is the alignment target mark 61. Further, the pupil shape (pupil diameter) in scotopia and that in photopia are numerically displayed as well as the information about the distance between the scotopic and photopic pupil center positions. The information about the scotopic and photopic pupil diameters may be utilized to determine the size of the ablation area.

The information thus obtained about the pupil in photopia and that in scotopia, and also about the differences between them, is stored in the storage part 45 along with the corneal ablation information. The stored information is outputted through a communication port 59b nor a floppy disc inserted in a floppy-disc drive 59a, and is then inputted to a computer included in a corneal surgery apparatus 200.

Incidentally, a mechanism of the refractive power measurement and that of the corneal shape measurement may be implemented individually in two separate ophthalmic apparatuses. Similarly, a mechanism of picking up the anterior segment image in scotopia and a mechanism of picking up that in photopia may also be implemented individually in two separate ophthalmic apparatuses. In addition, in such cases, the computation of the corneal ablation information based on the measurement data and the pupil information by image processing may be conducted using a personal computer (the ophthalmic apparatus having the ablation information computation part 54, the pupil information computation part 53, input means such as the mouse 57, the keyboard 58, the communication port 59b and the FDD 59a, output means such as the communication port 59b and the FDD 59a and the monitor 39, and others shown in FIG. 3). The measurement data and the anterior segment images picked up in photopia and scotopia are inputted to the personal computer, which displays (outputs) the computation result on (to) the monitor 39.

Figure 8:
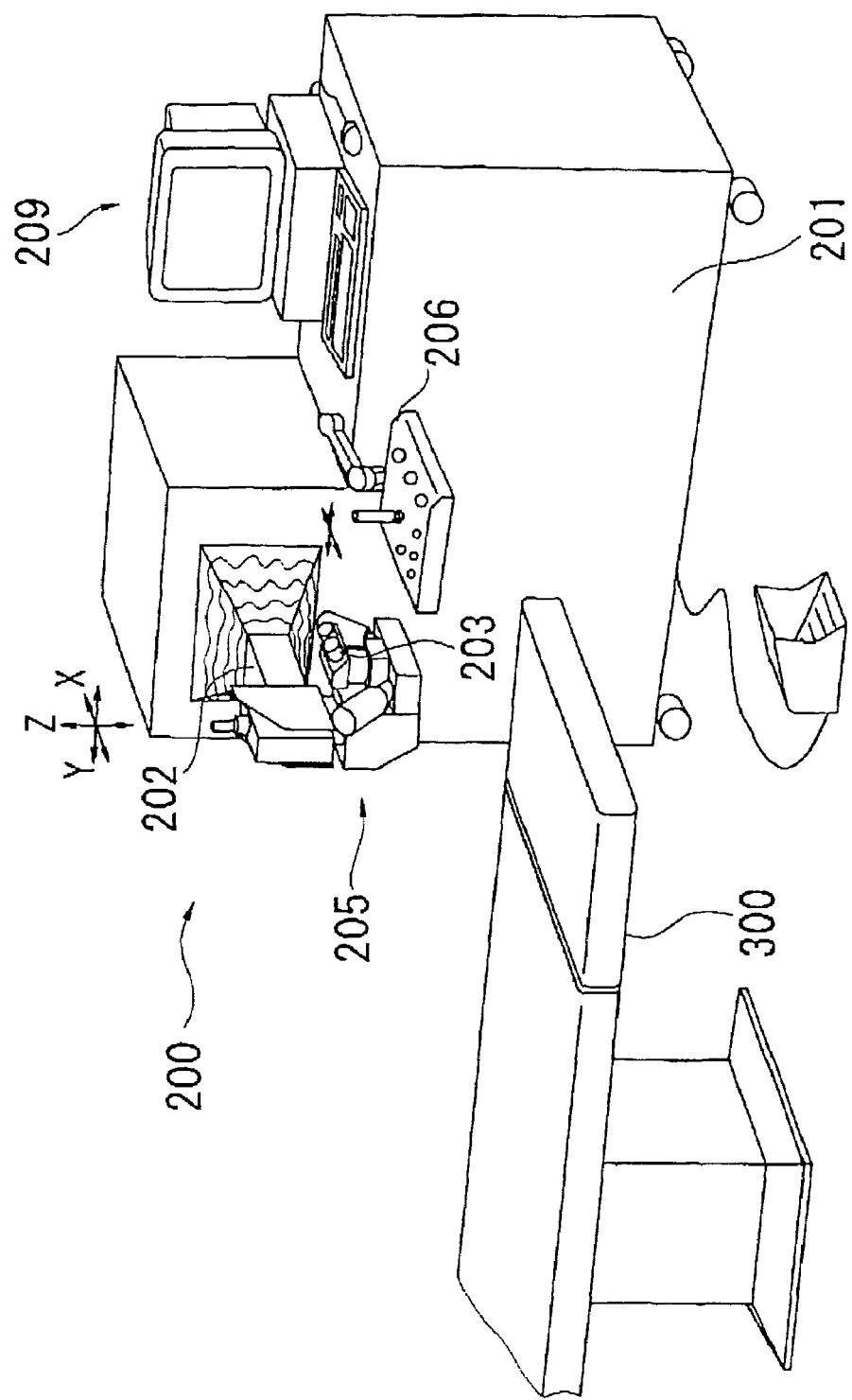
FIG. 8 is a view schematically showing an external configuration of a corneal surgery apparatus consistent with the present invention.
Figure 9:
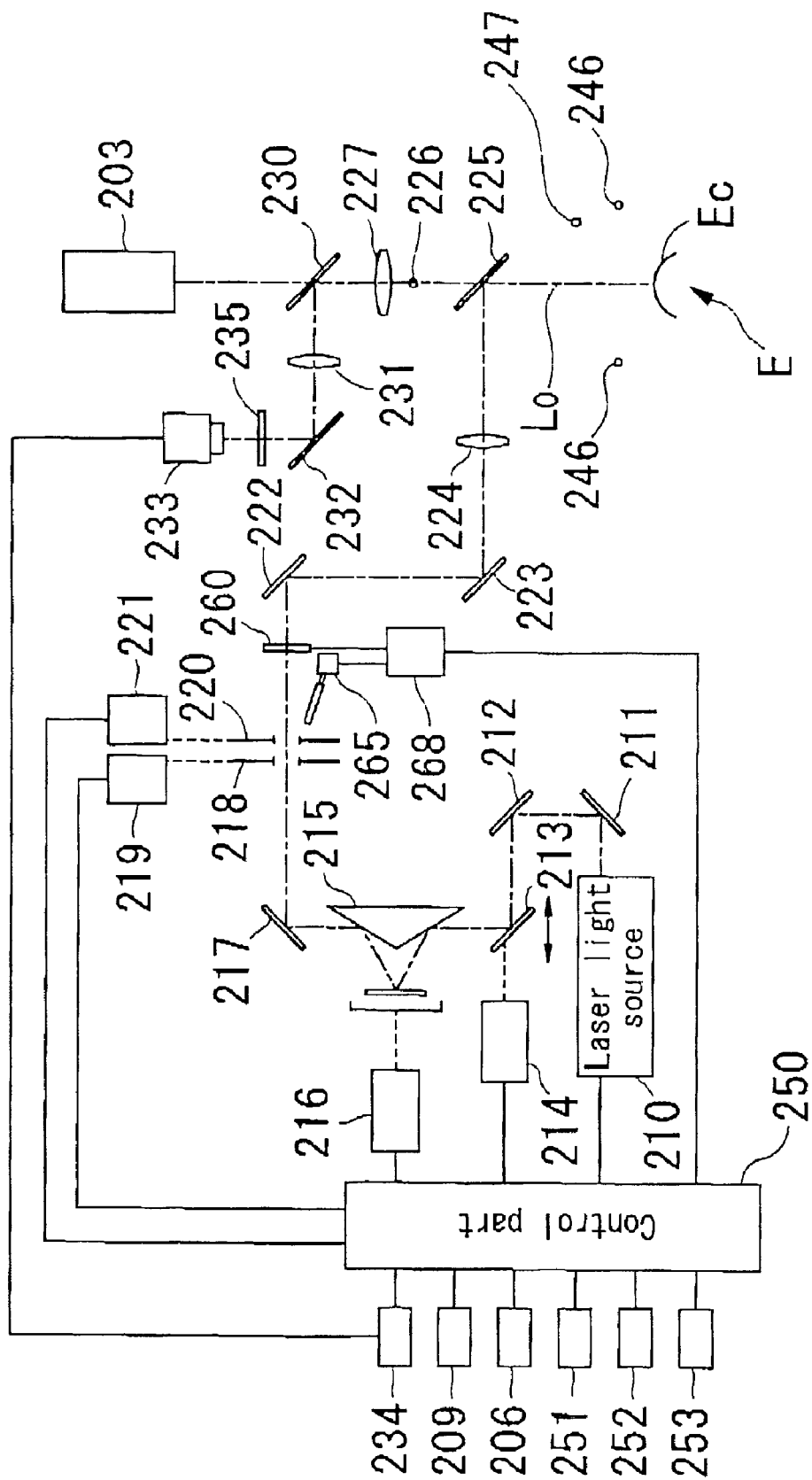
FIG. 9 is a view schematically showing a structure of an optical system included in the corneal surgery apparatus.

Next, the corneal surgery apparatus 200 will be described. FIG. 8 is a schematic external view of the corneal surgery apparatus 200, and FIG. 9 shows the structure of its optical system.

The laser beam from an excimer laser light source 210 placed inside a surgery apparatus main body 201 passes through a laser irradiation optical system including mirrors and the like, and is directed to an arm unit 202 which is movable in X and Y directions shown in FIG. 8. An arm-tip portion 205 is movable in a Z direction. Driving units 251, 252 and 253 constituted of motors and the like bring about movements in those directions. A controller 206 includes a joystick and a variety of switches. A computer 209 is capable of inputting various data about conditions required for surgery as well as computing, displaying and storing data about laser irradiation control. On a bed 300 for a patient, the patient undergoes surgery while he is lying down on the bed 300.

The laser irradiation optical system includes mirrors 211 and 212, a scan mirror 213 (a plane mirror which translates (moves) the laser beam in the direction of the Gaussian distribution), an image rotator 215, a mirror 217, a variable circular aperture 218, a variable slit aperture 220, mirrors 222 and 223, a projecting lens 224, and a dichroic mirror 225. A dividing aperture plate 260 having a plurality of small circular apertures is placed on an optical path between the slit aperture 220 and the mirror 222, and is configured to be removable from and insertable into the optical path. The dividing aperture plate 260 is configured to selectively divide the laser beam in combination of a dividing shutter 265. The small circular apertures of the dividing aperture plate 260 are selectively covered and uncovered by shutter plates of the dividing shutter 265. This enables selective division of the rectangle-shaped laser beam in the longitudinal direction during the laser irradiation. The dividing aperture plate 260 and the dividing shutter 265 may be moved in a plane normal to the axis of the laser beam by the driving unit 268.

Placed above the dichroic mirror 225 are a fixation lamp 226, an objective lens 227, and a microscope unit 203. A visible light source 247 illuminates the eye E, and a surgeon observes the eye E through the microscope unit 203. A mirror 230 is placed between binocular optical paths of the microscope unit 203 (on an optical axis of the objective lens 227). On an optical path on the reflecting side of the mirror 230, an image-forming lens 231, a mirror 232, an infrared light transmission filter 235 and a CCD camera 233 are arranged in the order in which they are mentioned above. The camera 233 picks up the anterior segment image of the eye E illuminated by an infrared light source 246. The output of the camera 233 is connected to an image processing part 234. Reference letter $L_0$ indicates a reference axis of irradiation of the laser beam.

One of the switches included in the controller 206 is operated to select an automatic alignment mode and/or an automatic tracking mode. The image processing part 234 conducts the same process as shown in FIGS. 6A and 6B based on the anterior segment image picked up by the camera 233, thereby obtaining (detecting) the pupil center position of the eye E. The eye E is in photopia since the corneal surgery apparatus 200 is used in a well-lighted room and the eye E is illuminated by the visible illumination light source 247. Therefore, the pupil center position obtained at the time of surgery is the pupil center position in photopia. A control part 250 performs alignment by controlling movement of the arm unit 202 relative to the obtained pupil center position. At this point, based on the information for correcting the alignment position inputted to the computer 209, the control part 250 offsets the reference axis $L_0$ of irradiation with respect to the pupil center position so that the reference axis L may be aligned with the pupil center position in scotopia. Based on the corneal ablation information, the control part 250 controls driving units 214, 216, 219 and 221, the driving unit 268 and others for the scan mirror 213, the image rotator 215, the variable circular aperture 218, the variable slit aperture 220, the dividing aperture plate 260, the dividing shutter 265, respectively, thereby irradiating the eye E with the laser beam. If the eye E moves, the arm unit 202 is moved based on the obtained pupil center position, whereby automatic tracking is performed.

Thus, the alignment position of the laser beam is offset from the pupil center position in photopia to the pupil center position in scotopia. This makes it possible to ablate an area predetermined based on the scotopic pupil center position. Therefore, such ablation may prevent a halo, glare or the like, which is apt to occur at night after surgery, with more reliability than the ablation in alignment with the photopic pupil center position.

In addition, the eye E rotates since the refractive surgery is conducted as the patient is lying down (on his back). Accordingly, ablation may be performed more accurately if information about the rotation (torsion) of the eye E which occurs when the patient lies on his back (rotation angle information) is added to the corneal ablation information for the same eye E which is obtained when he is seated. The surgeon obtains an angle of the eye rotation in advance based on the conditions of the eye E when the patient is seated and when he is lying down on his back, and this information is then inputted to the computer 209. Alternatively, it is also possible to extract characteristics of the anterior segment image which is picked up when the patient is seated, and then, to compare it with the anterior segment image picked up when he is lying down on his back, thereby obtaining the rotation angle of the eye E. The description of the present embodiment implies that an inclination of the patient's head at the time of image-pickup may be ignored in the anterior segment image in photopia and that in scotopia. However, if it is desired to compensate for the inclination, the aforementioned method for extracting the characteristics of the anterior segment images is followed, so that the anterior segment image in photopia and that in scotopia are corrected for the inclination, and a series of procedures may be executed thereafter.

Further, in the present embodiment, the anterior segment image in scotopia is picked up at the time of eye refractive power measurement, and the anterior segment image in photopia is picked up at the time of corneal shape measurement, but the present invention is not limited thereto. For example, the apparatus may be configured to have alternative modes of picking up the anterior segment images, one of which is specific for photopia and the other for scotopia to be selected using the mode-selecting switch 40.

A description will now be given to the case of providing the alternative modes specific for picking up the anterior segment images. For instance, in the image-pickup mode for scotopia, the light intensity of the light source 30 for eye-fixation is reduced within a range that allows the patient to gaze at the fixation point, while the light source 103 for corneal shape measurement is switched off, and thus the pupil of the eye E may be dilated. On the other hand, in the image-pickup mode for photopia, the light intensity of the light source 103 and that of the light source 30 may be set to cause myosis in the same degree as that in refractive surgery. It should be noted that the visible light source is not limited to the light sources 103 and 30. For example, the light source 103 may be a near infrared light source, and another light source may be provided as a visible light source instead.

Furthermore, in the present embodiment, the alignment target image 61 on the cornea Ec is aligned with the image-pickup axis when the anterior segment image is picked up, but the present invention is not limited thereto; it is also possible to use a method by which the image-pickup axis is aligned with the pupil center position when the anterior segment image is picked up. Hereinafter, a description will be given to a method for obtaining the information for correcting the alignment position under the method by which the image-pickup axis is aligned with the pupil center position at the time of picking up the image. Here, it is assumed that the ophthalmic apparatus adopted in the aforementioned embodiment is used.

First, the image-pickup axis is aligned with the scotopic pupil center position displayed on the monitor 39 through visual observations, and the anterior segment image is then picked up. The pupil information computation part 53 detects boundaries of the cornea Ec (a corneal outline) by conducting image processing on the picked-up anterior segment image in scotopia, and obtains the central coordinates of the corneal boundaries. Next, the pupil information computation part 53 obtains the scotopic pupil center position in the picked-up image by the same method as in the aforementioned embodiment. At this point, the pupil information computation part 53 computes the scotopic pupil center position with respect to the central coordinates calculated from the corneal outline.

Next, the anterior segment image in photopia is picked up, and the photopic pupil center position is obtained with respect to the central coordinates calculated from the corneal outline by the same method. The center of the corneal outline obtained from the anterior segment image of the scotopic eye is made to coincide with that of the photopic eye, thereby computing the distance between the scotopic and photopic pupil center positions. The distance thus obtained may be used as the information for correcting the alignment position in the same manner as in the aforementioned embodiment.

Moreover, the present embodiment has been described taking the ophthalmic apparatus capable of measuring both eye refractive power and a corneal shape as an example, but the present invention is not limited thereto. Any other ophthalmic apparatus may be used as long as it is capable of obtaining pupil information in scotopia and that in photopia.

What is more, the present invention allows not only obtaining the information about the pupil position, but also obtaining the pupil diameter (pupil shape) in scotopia and that in photopia. The obtained pupil diameters may therefore be used for designing a contact lens or other purposes. For example, take a multifocal contact lens in which curved surfaces having diopters for far vision and those having diopters for near vision are formed alternately in concentric circles around the lens geometric center; such a lens may be designed to have its optical center deviated from the lens geometric center in consideration of the pupil diameter and the pupil center position in scotopia and those in photopia.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:

an illumination unit which illuminates an anterior segment including a pupil of a patient's eye with visible light;

a light intensity adjustment unit which adjusts light intensity of the visible light;

the light intensity adjustment unit increasing the light intensity of the visible light in a first mode and decreasing the light intensity of the visible light in a second mode:

an image-pickup unit which picks up an image of the anterior segment, the image-pickup unit picking up a first image of the anterior segment of the eye in photopia of which the pupil is constricted in the same degree as myosis in refractive surgery with visible light illumination by increasing the light intensity of the visible light in the first mode, and picking up a second image of the anterior segment of the eye in scotopia of which the pupil is dilated in the same degree as natural mydriasis in a dark place by decreasing the light intensity of the visible light in the second mode;

a pupil information computation unit which obtains pupil information in each of the first and second images by image processing, the pupil information including at least one of a position and a shape of the pupil, and obtains information about a difference between the pupil information in the first image and the pupil information in the second image; and output means for outputting the obtained information about the difference.

2. The ophthalmic apparatus according to claim 1, wherein:

the pupil information computation unit obtains a position of a pupil center in each of the first and second images, and obtains information about a positional difference between the pupil center position in the first image and the pupil center position in the second image; and the output means outputs the obtained information about the positional difference.

3. The ophthalmic apparatus according to claim 1, wherein the output means includes a display unit which graphically displays the obtained pupil information and the obtained information about the difference.

4. A corneal surgery apparatus to be used in refractive surgery, for ablating a cornea by laser beam irradiation, the apparatus comprising:

a laser irradiation unit which irradiates a cornea of a patient's eye with a laser beam, the irradiation unit including a optical system;

an alignment unit which aligns an irradiation position of the laser beam with the eye;

position input means for inputting information about a positional difference between a pupil position of the eye in photopia of which a pupil of the eye is constricted in the same degree as myosis in the refractive surgery with visible light illumination and a pupil position of the eye in scotopia of which the pupil is dilated in the same degree as natural mydriasis in a dark place;

an image-pickup unit which picks up an image of an anterior segment including the pupil of the eye;

a pupil position detection unit which detects a pupil position of the eye in the refractive surgery from the anterior segment image picked up by the image-pickup unit in the refractive surgery;

a position computation unit which obtains information about an alignment position based on the detected pupil position and the inputted information about the positional difference; and an alignment control unit which controls the alignment unit based on the obtained information about the alignment position.

5. The corneal surgery apparatus according to claim 4, further comprising:

shape input means for inputting a pupil shape of the eye in the photopia and a pupil shape of the eye in the scotopia;

an area computation unit which obtains a size of an ablation area based on each of the inputted pupil shapes; and an irradiation control unit which controls the irradiation unit based on the obtained size of the ablation area.

6. The corneal surgery apparatus according to claim 4, further comprising:

an illumination unit which illuminates the anterior segment with the visible light.

* * * * *